(12) United States Patent
Glenn (10) Patent No.: US 9,138,563 B2
(45) Date of Patent: Sep. 22, 2015

(54) SUBCUTANEOUS CATHETER RETAINER

(75) Inventor: Bradley J. Glenn, Oneida, WI (US)

(73) Assignee: Stealth Therapeutics, Inc., Madison, WI (US)

( * ) Notice: Subject to any disclaimer, the term of this patent is extended or adjusted under 35 U.S.C. 154(b) by 742 days.

(21) Appl. No.: 11/731,172

(22) Filed: Mar. 30, 2007

(65) Prior Publication Data

US 2007/0232997 A1 Oct. 4, 2007

Related U.S. Application Data

(60) Provisional application No. 60/787,508, filed on Mar. 31, 2006, provisional application No. 60/802,127, filed on May 22, 2006.

(51) Int. Cl.
*A61M 25/00* (2006.01)
*A61M 25/04* (2006.01)
*A61B 17/34* (2006.01)
*A61M 25/02* (2006.01)

(52) U.S. Cl.
CPC ............ *A61M 25/04* (2013.01); *A61B 17/3421* (2013.01); *A61M 25/02* (2013.01); *A61B 2017/3484* (2013.01)

(58) Field of Classification Search
CPC ..................... A61M 25/04; A61M 2025/0233; A61M 2025/0213; A61M 2025/0286
USPC ............... 604/103.03, 104, 105, 164.01, 523, 604/106–109, 17; 606/192, 194, 200, 244
See application file for complete search history.

(56) References Cited

U.S. PATENT DOCUMENTS

| | | | | | |
|---|---|---|---|---|---|
| 837,085 | A | * | 11/1906 | Loar | 604/108 |
| 1,434,964 | A | * | 11/1922 | Rose | 604/108 |
| 1,733,189 | A | * | 10/1929 | Friedman | 604/104 |
| 3,397,699 | A | * | 8/1968 | Kohl | 604/105 |
| 3,692,029 | A | * | 9/1972 | Adair | 604/105 |
| 3,713,447 | A | * | 1/1973 | Adair | 604/105 |

(Continued)

FOREIGN PATENT DOCUMENTS

WO     WO 95/12427     5/1995

OTHER PUBLICATIONS

James C. Andrews, MD et al.; Long-Term Central Venous Access with a Peripherally Placed Subcutaneous Infusion Port: Initial Results; Radiology; Jul. 1990; pp. 45-47; vol. 176, No. 1.

(Continued)

*Primary Examiner* — Bhisma Mehta
*Assistant Examiner* — Bradley Osinski
(74) *Attorney, Agent, or Firm* — Heisler & Associates (57) ABSTRACT

A retainer is provided which can be affixed to a medical tube, such as a catheter, or formed with the tube. The retainer has a base portion which is fixed to the tube. An expandable width portion is coupled to the base portion. This expandable width portion can transition between a collapsed configuration and an expanded configuration, with the expanded configuration wider than the base portion and the collapsed configuration narrower than the expanded configuration. This retainer is located on a portion of the tube which is subcutaneous but near the skin. After the tube is positioned where desired, the retainer is transitioned from the collapsed configuration to the expanded configuration. The retainer then resists removal of the tube, due to the expanded width of the retainer and its location beneath the skin. The tube fitted with the retainer can be a PICC line or other form of medical tube.

13 Claims, 7 Drawing Sheets

(56) References Cited

U.S. PATENT DOCUMENTS

| Patent No. | | Date | Inventor | Ref |
|---|---|---|---|---|
| 3,938,530 | A * | 2/1976 | Santomieri | 604/105 |
| 3,951,147 | A | 4/1976 | Tucker | |
| 4,043,338 | A * | 8/1977 | Homm et al. | 604/105 |
| 4,077,412 | A * | 3/1978 | Moossun | 604/103.03 |
| 4,543,088 | A | 9/1985 | Bootman | |
| 4,569,675 | A | 2/1986 | Prosl | |
| 4,604,090 | A | 8/1986 | Reinicke | |
| 4,608,965 | A * | 9/1986 | Anspach et al. | 600/101 |
| 4,626,244 | A | 12/1986 | Reinicke | |
| 4,627,838 | A * | 12/1986 | Cross et al. | 604/105 |
| 4,673,394 | A | 6/1987 | Fenton, Jr. | |
| 4,704,103 | A | 11/1987 | Stober | |
| 4,743,231 | A | 5/1988 | Kay | |
| 4,772,270 | A | 9/1988 | Wiita | |
| 4,778,452 | A | 10/1988 | Moden | |
| 4,802,885 | A | 2/1989 | Weeks | |
| 4,880,414 | A | 11/1989 | Whipple | |
| 4,995,868 | A * | 2/1991 | Brazier | 604/105 |
| 5,090,954 | A | 2/1992 | Geary | |
| 5,092,849 | A | 3/1992 | Sampson | |
| 5,108,377 | A | 4/1992 | Cone | |
| 5,112,310 | A * | 5/1992 | Grobe | 604/175 |
| 5,113,846 | A * | 5/1992 | Hiltebrandt et al. | 600/225 |
| 5,167,638 | A | 12/1992 | Felix | |
| 5,215,103 | A * | 6/1993 | Desai | 606/46 |
| 5,217,450 | A * | 6/1993 | Pryor et al. | 604/891.1 |
| 5,217,451 | A * | 6/1993 | Freitas | 606/1 |
| 5,275,610 | A * | 1/1994 | Eberbach | 606/198 |
| 5,279,565 | A * | 1/1994 | Klein et al. | 604/105 |
| 5,306,226 | A * | 4/1994 | Salama | 600/29 |
| 5,332,398 | A | 7/1994 | Miller | |
| 5,338,297 | A * | 8/1994 | Kocur et al. | 604/103.03 |
| 5,344,439 | A * | 9/1994 | Otten | 607/126 |
| 5,356,382 | A * | 10/1994 | Picha et al. | 604/105 |
| 5,360,407 | A | 11/1994 | Leonard | |
| 5,365,926 | A * | 11/1994 | Desai | 600/374 |
| 5,387,192 | A | 2/1995 | Glantz | |
| 5,399,168 | A | 3/1995 | Wadsworth, Jr. | |
| 5,421,832 | A * | 6/1995 | Lefebvre | 264/173.11 |
| 5,443,449 | A * | 8/1995 | Buelna | 604/105 |
| 5,454,365 | A * | 10/1995 | Bonutti | 600/204 |
| 5,527,336 | A * | 6/1996 | Rosenbluth et al. | 606/192 |
| 5,547,458 | A * | 8/1996 | Ortiz et al. | 600/204 |
| 5,562,618 | A | 10/1996 | Cai | |
| 5,624,395 | A * | 4/1997 | Mikhail et al. | 604/99.04 |
| 5,624,399 | A * | 4/1997 | Ackerman | 604/103.03 |
| 5,632,729 | A | 5/1997 | Cai | |
| 5,688,247 | A | 11/1997 | Haindl | |
| 5,716,326 | A | 2/1998 | Dannan | |
| 5,833,654 | A | 11/1998 | Powers | |
| 5,848,989 | A | 12/1998 | Villani | |
| 5,906,596 | A | 5/1999 | Tallarida | |
| 5,957,900 | A * | 9/1999 | Ouchi | 604/264 |
| 5,971,954 | A * | 10/1999 | Conway et al. | 604/101.05 |
| 5,989,216 | A | 11/1999 | Johnson | |
| 5,990,382 | A | 11/1999 | Fox | |
| 6,030,406 | A * | 2/2000 | Davis et al. | 606/198 |
| 6,080,142 | A * | 6/2000 | Sachse | 604/544 |
| 6,099,506 | A * | 8/2000 | Macoviak et al. | 604/173 |
| 6,190,352 | B1 | 2/2001 | Haarala | |
| 6,213,973 | B1 | 4/2001 | Eliasen | |
| 6,355,020 | B1 | 3/2002 | Bousquet | |
| 6,409,674 | B1 | 6/2002 | Brockway | |
| 6,485,473 | B1 | 11/2002 | Lynn | |
| 6,569,150 | B2 * | 5/2003 | Teague et al. | 604/524 |
| 6,572,587 | B2 | 6/2003 | Lerman | |
| 6,601,795 | B1 | 8/2003 | Chen | |
| 6,623,448 | B2 * | 9/2003 | Slater | 604/95.01 |
| 6,629,953 | B1 * | 10/2003 | Boyd | 604/106 |
| 6,629,956 | B1 | 10/2003 | Polidoro | |
| 6,695,861 | B1 * | 2/2004 | Rosenberg et al. | 606/185 |
| 6,699,216 | B2 * | 3/2004 | Ikeguchi | 604/96.01 |
| 6,758,831 | B2 * | 7/2004 | Ryan | 604/103.03 |
| 6,780,175 | B1 | 8/2004 | Sachdeva et al. | 604/531 |
| 6,893,418 | B2 * | 5/2005 | Liu | 604/106 |
| 6,929,621 | B2 * | 8/2005 | Whitmore et al. | 604/109 |
| 6,997,885 | B2 * | 2/2006 | Lubock et al. | 600/567 |
| 6,997,909 | B2 * | 2/2006 | Goldberg | 604/175 |
| 6,997,914 | B2 | 2/2006 | Smith | |
| 7,037,321 | B2 * | 5/2006 | Sachdeva et al. | 606/200 |
| 2001/0049492 | A1 * | 12/2001 | Frazier et al. | 604/104 |
| 2002/0165553 | A1 * | 11/2002 | Elbert et al. | 606/108 |
| 2002/0177806 | A1 * | 11/2002 | Meier et al. | 604/104 |
| 2002/0177814 | A1 | 11/2002 | Meng | |
| 2003/0014009 | A1 * | 1/2003 | Kletschka | 604/104 |
| 2004/0078004 | A1 | 4/2004 | Bourne | |
| 2004/0249342 | A1 * | 12/2004 | Khosravi et al. | 604/96.01 |
| 2004/0254537 | A1 | 12/2004 | Conlon | |
| 2005/0043735 | A1 | 2/2005 | Ahmad | |
| 2005/0075644 | A1 | 4/2005 | DiPoto | |
| 2005/0113929 | A1 | 5/2005 | Cragg | |
| 2005/0119617 | A1 * | 6/2005 | Stecker et al. | 604/104 |
| 2005/0131383 | A1 | 6/2005 | Chen | |
| 2005/0177105 | A1 * | 8/2005 | Shalev | 604/104 |
| 2005/0251168 | A1 * | 11/2005 | Hess et al. | 606/153 |
| 2006/0217673 | A1 | 9/2006 | Schulze | |
| 2007/0088258 | A1 * | 4/2007 | Wenchell et al. | 604/104 |
| 2007/0088259 | A1 * | 4/2007 | Chu et al. | 604/104 |
| 2007/0276493 | A1 * | 11/2007 | Malandain et al. | 623/17.11 |

OTHER PUBLICATIONS

Ernst-Peter K. Strecker, MD et al.; Percutaneously Implantable Catheter-Port System: Preliminary Technical Results; Radiology; Feb. 1997; pp. 574-577; vol. 202, No. 2.

Hyoung Il NA, MD et al.; Fixation Methods for Implantable Port Chamber: Comparative Study Using Glue, Self-Stabilizing Leg and Suture Fixations in Rabbits; Korean J Radiol 5(4); Dec. 2004, pp. 266-273.

* cited by examiner

SUBCUTANEOUS CATHETER RETAINER

CROSS-REFERENCE TO RELATED APPLICATIONS

This application claims benefit under Title 35, United States Code §119(e) of U.S. Provisional Application No. 60/787,508 filed on Mar. 31, 2006 and U.S. Provisional Application No. 60/802,127 filed on May 22, 2006.

FIELD OF THE INVENTION

The following invention relates to catheters, and other medical tubes, most typically to peripherally inserted central catheters (often called "PICC lines") which are adapted to be implanted with a discharge end thereof within a body lumen and an access portion which is outside of the skin of the patient, such that the medical tube has a subcutaneous portion and a portion outside of the skin. More particularly, this invention relates to PICC lines and other medical tubes which include a retainer on subcutaneous portions thereof to resist removal of the PICC line or other medical tube from the patient.

BACKGROUND OF THE INVENTION

Peripherally inserted central catheters, often referred to as "PICC lines," are used to provide a convenient interface with a patient's circulatory system for delivery of medications and other substances into the patient. Such catheters generally include an intraluminal portion, a subcutaneous portion and a portion outside of the skin. Other medical tubes akin to catheters are also known in the prior art, such as vascular access sheaths and cannulas. The retainer of this invention can be fitted to or formed with any of these medical tubes to function according to this invention. The term catheter is thus considered to broadly include any medical tube.

Medical tubes are generally configured as an elongate conduit extending from a discharge end to an access end. The discharge end is implanted inside a body lumen, such as a large patient vein. The access end typically includes an interface thereon which can be coupled to various different fluid delivery devices, such as infusion pumps, or syringe accepting interfaces, most typically those having a "luer lock" type fitting (and less commonly a septum that can be penetrated by a needle to gain access into an interior of the medical tube).

One problem with such medical tubes is that they can be inadvertently removed, such as if forces tugging at a portion of the medical tube outside of the body occur sufficient to dislodge the medical tube. When such an event occurs, the medical tube must be repositioned by medical personnel, and can potentially pose a danger to the patient. Most commonly catheters of this type are held in place merely by taping a portion of the catheter outside of the body against the patient's skin. This arrangement disadvantageously requires that the tape or other bandage be carefully maintained and is not as effective as desired in preventing undesirable removal of the medical tube.

Accordingly, a need exists for a catheter medical tube that is subcutaneous and can hold the medical tube in a manner resisting removal of the medical tube from the patient until such removal is desired.

SUMMARY OF THE INVENTION

With this invention a subcutaneous catheter or other medical tube retainer is provided which can either be integrated into the manufacture of the medical tube itself or can be attached to any of a variety of prior art medical tubes. The retainer provides the general function of keeping the medical tube in position and preventing the medical tube from being pulled and removed out of the patient at the implantation site.

The retainer generally has two portions including a base portion and an expandable width portion. The base portion can either be a structure removably attachable to the medical tube or a portion built into the medical tube itself. In either event, the base portion remains affixed to the medical tube during use of the retainer according to this invention. The expandable width portion of the retainer can be provided in a variety of different embodiments as disclosed herein.

Generally, the expandable width portion has at least two configurations including a collapsed configuration and an expanded configuration. The expanded configuration exhibits a width greater than a width of the base portion. Thus, the medical tube can be implanted through an incision in the skin to a subcutaneous location while in the collapsed configuration. The expandable width portion of the retainer can then be transitioned to the expanded configuration and have a width potentially greater than a width of the incision, such that the medical tube and associated retainer cannot be removed through the same incision, but rather is held subcutaneously by the retainer bumping up against an underside of the skin of the patient.

The collapsed configuration for the expandable width portion has a lesser width than the expanded configuration. Thus, this collapsed configuration provides a most convenient configuration for the implanting of the retainer along with the medical tube into the subcutaneous location. Control devices are also provided to cause the retainer to transition from the collapsed configuration to the expanded configuration after location of the retainer into the subcutaneous location, under direction of the appropriate medical practitioner.

Removal can occur by reversing the expansion transition. In particular, the medical practitioner causes a transition from the expanded configuration to the collapsed configuration for the retainer. The medical tube and associated retainer can then be more easily removed through the incision in the skin of the patient.

In a first embodiment, the retainer is in the form of a pair of sleeves with wings interposed between the sleeves. One of the sleeves is a fixed sleeve acting as the base portion of the retainer. This fixed sleeve is adapted to be fixed to the catheter or other medical tube either permanently or in a removably attachable manner, depending on whether the retainer is retrofitted onto an existing catheter or manufactured along with the formation of the catheter. The sliding sleeve slides relative to the fixed sleeve. The wings between the sliding sleeve and the fixed sleeve have links which can either be oriented substantially linearly along a long axis of the catheter when the sliding sleeve is distant from the fixed sleeve, or be pivoted to an orientation lateral to this long axis of the catheter by sliding the sliding sleeve toward the fixed sleeve.

A handle is preferably coupled to the sliding sleeve which can extend through the incision site or remain just outside of the skin of the patient to allow sliding of the sliding sleeve along the catheter. This handle is preferably in the form of a semi-circle that can clamp onto the portion of the catheter outside of the skin. The handle has a length equal to a distance from the sliding sleeve to the hub of the catheter, when the wings are in their expanded configuration, to hold the sliding sleeve and the wings in their expanded configuration. In this embodiment, the wings provide one form of the expandable width portion of the retainer.

In a second type of retainer embodiment, a post is formed with the catheter or other medical tube or made to attach to the catheter with the post extending non-parallel with a long axis of the catheter. A leg or other elongate structure is pivotably supported upon this post. This leg has a first position defining a collapsed form extending substantially parallel with the long axis of the catheter and can pivot to a second position in an orientation transverse to this long axis of the catheter to provide an expanded form. In this embodiment the leg acts as the expandable width portion of the retainer. The post acts as the base portion of the retainer. The leg can either be straight or bent slightly in various different embodiments. The catheter can include ramps above and below the leg when in the collapsed form, to keep the leg from catching on the skin or other body structures during implantation or removal of the catheter and associated retainer.

In a third form of retainer embodiment, the catheter or other medical tube can be formed with a base portion extending therefrom, typically underneath a conduit of the catheter, which includes a chamber that is substantially closed except for where slits extend laterally out of the chamber. An expandable width portion is located within this chamber which is configured to transition from a narrow form to a wide form.

This expandable width portion could for instance be in the form of an expansion loop which has multiple segments pivotably joined together and which can transition from a first orientation where the segments are generally aligned parallel with each other and with a narrowest form exhibited by the expansion loop, with the expansion loop substantially entirely within the chamber. Joints between the segments can pivot to transition the expansion loop into the wide form where the segments are substantially parallel with each other and transverse to a long axis of the catheter, with portions of the expansion loop extending out of the side slots of the chamber, so that an expanded configuration for the expandable width portion is provided.

As an alternative to such an expansion loop, an expansion shuttle can be provided having a pair of limbs hingedly coupled together. The limbs can be oriented substantially parallel and adjacent to each other to keep the shuttle entirely within the chamber in a collapsed configuration for the expandable width portion. The expansion shuttle can transition by having the limbs rotate to an orientation with each of the limbs extending away from each other, so that the limbs define an expanded configuration for the expansion shuttle, with the limbs extending out of the slots in the chamber and lateral to the long axis of the catheter.

The expansion loop, expansion shuttle or other expandable width portion within the chamber can be caused to transition between the collapsed configuration and the expanded configuration, such as by attaching a pull line to a portion of the expandable width portion so that when the pull line is pulled, the expandable width portion is caused to transition to the expanded configuration. Other tools, springs or other structures could also alternatively be provided to cause this transition to take place, or the expandable width portion could be configured to be manipulatable by hands of the medical practitioner to cause transition of the expandable width portion between the collapsed configuration and the expanded configuration.

OBJECTS OF THE INVENTION

Accordingly, a primary object of the present invention is to provide a medical tube, such as a PICC line, which has portions thereof which are subcutaneous and portions thereof which are outside of the body, and with a retainer located subcutaneously to keep the medical tube from becoming displaced.

Another object of the present invention is to provide a medical tube which can be easily held in precise subcutaneous position within a patient.

Another object of the present invention is to provide a subcutaneous retainer which is attachable to an existing medical tube.

Another object of the present invention is to provide a subcutaneous medical tube which has a retainer built into the medical tube to keep subcutaneous portions of the medical tube in a desired location.

Another object of the present invention is to provide a subcutaneous medical tube retainer which has at least two configurations including a collapsed configuration in which the medical tube can be easily implanted and an expanded configuration in which the medical tube is difficult to remove.

Other further objects of the present invention will become apparent from a careful reading of the included drawing figures, the claims and detailed description of the invention.

BRIEF DESCRIPTION OF THE DRAWINGS

FIG. 6 is a perspective view of that which is shown in FIG. 2, showing the retainer in its expanded configuration for the expandable width portion. Also, while FIG. 6 depicts the catheter extending to a hub past a tip of the handle, the handle would typically be sufficiently long to abut the hub, as shown in FIG. 2.

DESCRIPTION OF THE PREFERRED EMBODIMENT

Referring to the drawings, wherein like reference numerals represent like parts throughout the various drawing figures, reference numeral 10 (FIGS. 1 and 2) is directed to a subcutaneous medical tube retainer particularly configured for holding a catheter 20 in a subcutaneous location beneath skin S of a patient. Other embodiments could be provided where the catheter 20 is replaced with a vascular access sheath, cannula or other medical tube, and the retainer 10 would merely be modified in dimensions and/or materials to accommodate the medical tube being utilized.

Figures 1, 2:
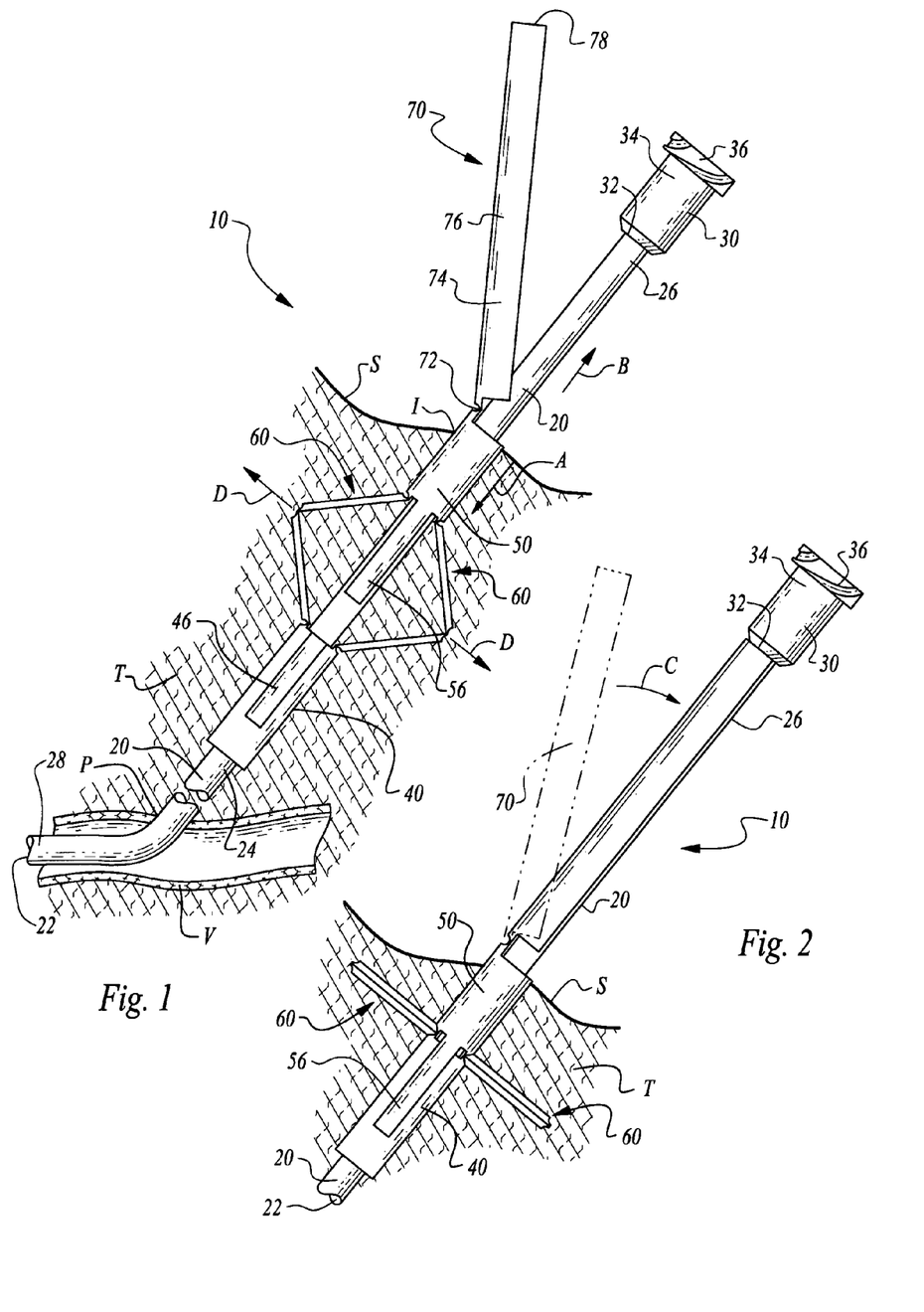
FIG. 1 is a side elevation view of the subcutaneous medical tube retainer of this invention in a preferred embodiment with the retainer shown in a form which is either attachable to the catheter or other medical tube or formed with the catheter. The catheter is shown implanted within a subcutaneous space in a body of a patient at the beginning of the process of transitioning an expandable width portion of the retainer from a collapsed configuration to an expanded configuration.
FIG. 2 is a side elevation view similar to that which is shown in FIG. 1, but after the expandable width portion has been fully expanded and a handle thereof has been closed to lock the expandable width portion in the expanded configuration.
Figure 3:
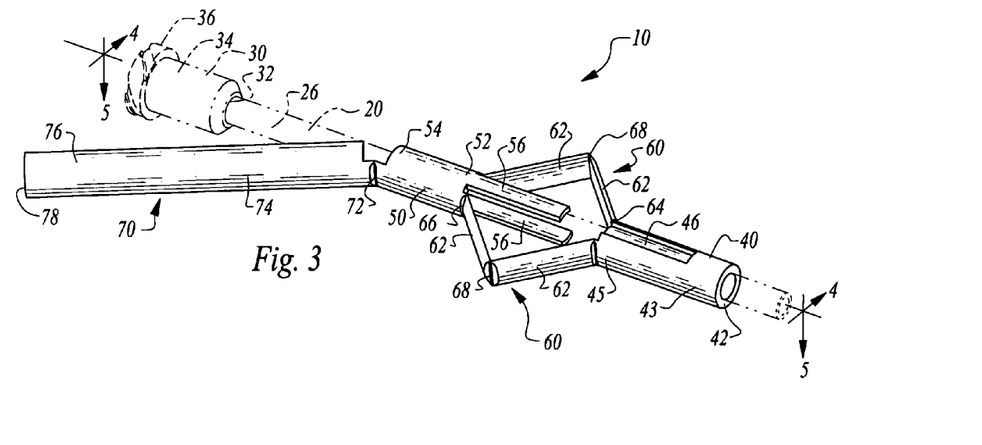
FIG. 3 is a perspective view of that which is shown in FIG. 1 and with the catheter shown in broken lines to allow details of the retainer to be more clearly shown.
Figure 4:
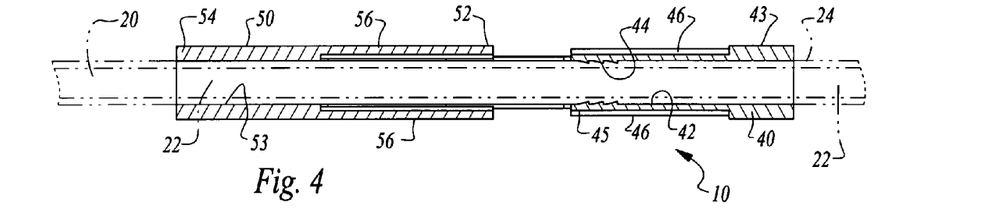
FIG. 4 is a full sectional view of that which is shown in FIG. 3, taken along lines 4-4 of FIG. 3.
Figure 5:
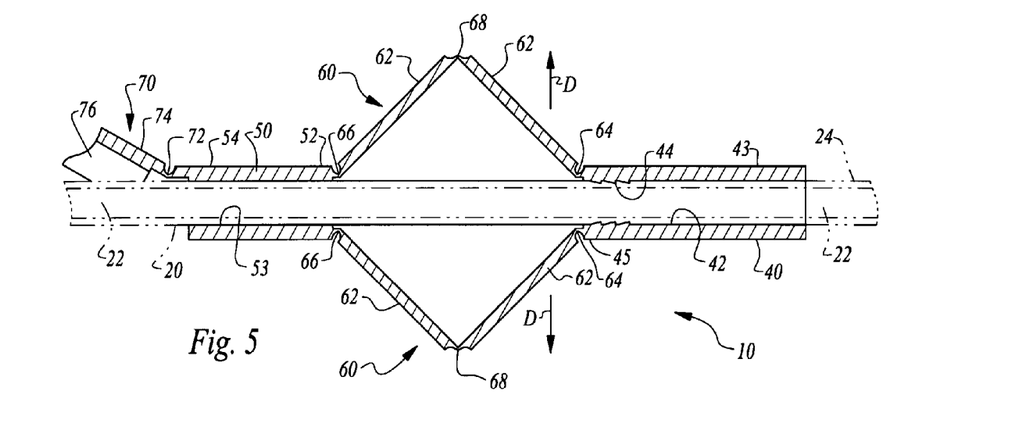
FIG. 5 is a full sectional view of that which is shown in FIG. 3, taken along lines 5-5 of FIG. 3.
Figure 6:
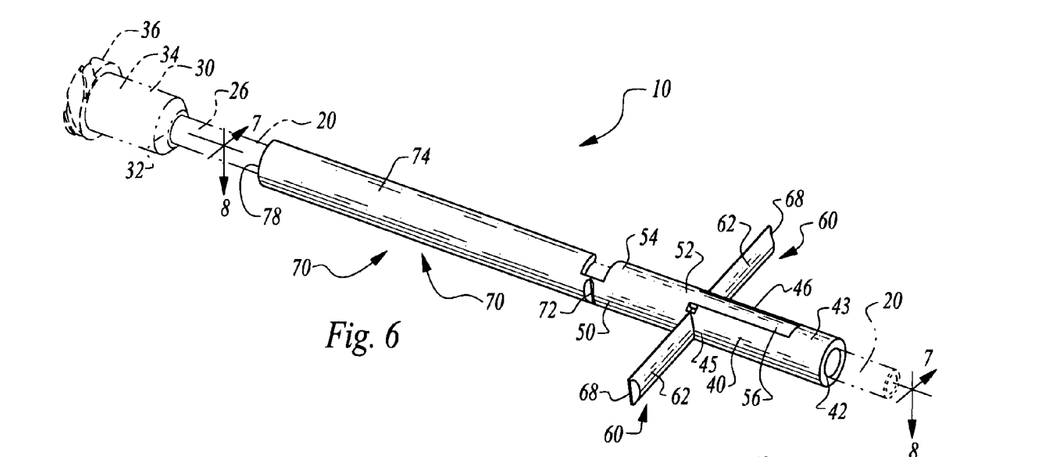
Figure 7:
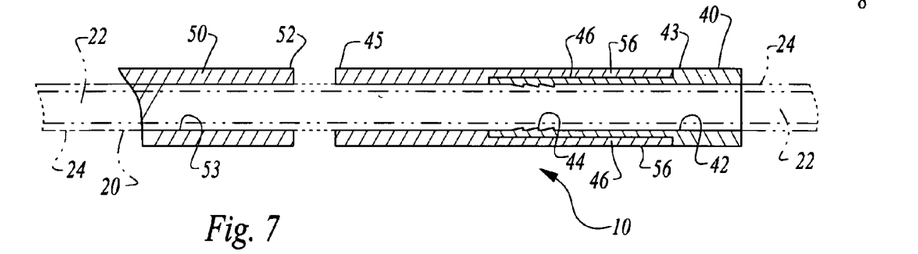
FIG. 7 is a full sectional view of a portion of that which is shown in FIG. 6, taken along lines of 7-7 of FIG. 6.
Figure 8:
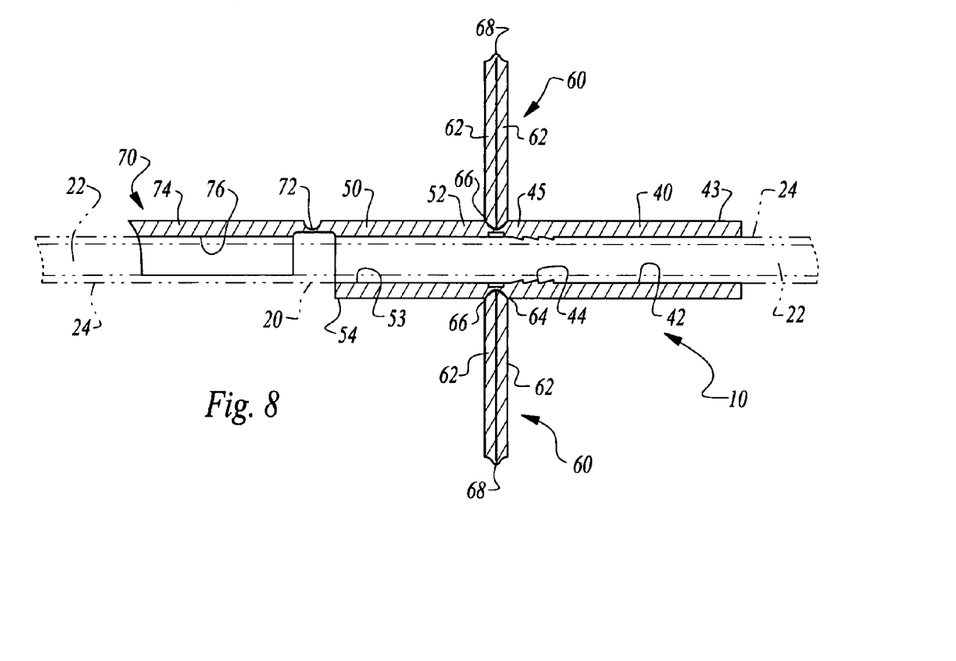
FIG. 8 is a full sectional view of a portion of that which is shown in FIG. 6, taken along lines 8-8 of FIG. 6.

The catheter 20 is implanted extending through an incision I in the skin S and through an entry point P in a vein V or other lumen. The retainer 10 is located subcutaneously, below the surface S, and can transition between a collapsed configuration and an expanded configuration. In the collapsed configuration the retainer 10 can be easily passed through the incision I in the skin S for convenient implantation of the catheter 20 along with the retainer 10. Once the retainer 10 transitions to the expanded configuration (along arrow D of FIG. 1, and as shown in FIG. 2) the catheter 20 and associated retainer 10 are held subcutaneously below the skin S and within tissues T below the surface S. The retainer 10 can be configured to removably attach to the catheter 20 or be configured to be built into the catheter 20 so that the retainer 10 becomes a feature of the catheter 20.

In essence and with particular reference to FIGS. 1-8, particular details of the retainer 10 are described according to a preferred embodiment. The catheter 20 is an elongate hollow structure with a subcutaneous portion which can be implanted into a vein V or other body lumen, and a portion which extends out of the body of the patient. A hub 30 is preferably located on an end of the catheter 20 outside of the patient's body. This hub 30 acts as an interface through which the catheter 20 can be coupled to other structures and devices, such as infusion pumps or syringes.

The retainer 10 includes a base portion either formed along with or affixable to the catheter, and an expandable width portion coupled to the base portion and transitioning between a collapsed configuration and an expanded configuration. In the preferred embodiment, the base portion includes a fixed sleeve 40 which can initially either slid over the catheter 20 and then later engages the catheter 20, such as through teeth 44, or the fixed sleeve 40 can be formed with the catheter 20 or otherwise bonded or mechanically fastened to the catheter 20 to hold the fixed sleeve 40 to the catheter 20.

Wings 60 are coupled to the fixed sleeve 40 and provide a preferred form of the expandable width portion of the retainer 10. The wings 60 are formed of multiple links 62 which pivot relative to each other and relative to the fixed sleeve 40 to transition the wings 60 from a collapsed configuration to an expanded configuration. A sliding sleeve 50 preferably is attached to the wings 60 on an end of the wings 60 spaced from the fixed sleeve 40. The sliding sleeve 50 has a bore 53 which also is oriented with the catheter 20 passing therethrough. The sliding sleeve 50 can slide along the catheter 20 to cause the wings 60 to transition from the collapsed configuration to the expanded configuration.

A handle 70 is coupled to the sliding sleeve 50. This handle 70 can be manipulated by a medical practitioner to cause the sliding sleeve 50 to slide along the catheter 20, and to cause the wings 60 to transition from the collapsed configuration to the expanded configuration. The handle 70 would remain outside of the patient's body while the wings 60 would remain subcutaneous.

More specifically, and with particular reference to FIGS. 1-8, particular details of the catheter 20 and hub 30 with which the retainer 10 would typically be associated are described, according to this preferred embodiment. The catheter 20 is an elongate structure with a hollow interior defining a conduit 22. This conduit 22 is surrounded by a wall 24 which is typically of constant thickness. The wall 24 is typically formed of a biocompatible plastic material which is somewhat flexible. By making the wall 24 somewhat flexible, the catheter 20 can be threaded along an interior of a vein V or other body lumen from an entry point P in the vein V or other lumen, to a location where medication or other substances are to be discharged within the circulatory system or other internal patient discharge location. This material forming the wall 24 also has at least some degree of stiffness so that it can generally be pushed as well as pulled to position the catheter 20 where desired, with the catheter 20 generally being flexible but not elastic to an appreciable degree.

The catheter 20 extends from an access end 26 to a discharge end 28. The discharge end 28 is that end of the catheter 20 which is typically implanted within a vein V or other body lumen. The access end 26 typically remains outside of the skin S of the patient. The retainer 10 is typically attached to the catheter 20 at a point between the access end 26 and discharge end 28, which is that portion of the catheter 20 which is close to the skin S but subcutaneous within the body of the patient.

The hub 30 is coupled to the catheter 20 at the access end 26. The hub 30 acts as an interface to which adjacent medication delivery devices can be attached. This hub 30 generally includes a step 32 defining a transition in diameter from a diameter of the wall 24 of the catheter 20 to a diameter of the hub 30. The hub 30 is typically cylindrical in form with a cylinder 34 extending from the step 32 to a threaded rim 36. The threaded rim 36 is typically slightly greater in diameter than the cylinder 34.

This threaded rim 36 is most preferably threaded with broad high pitch threads similar to those utilized in a "luer lock" type attachment system, such as is commonly provided on the ends of syringes and other medical tubing. This threaded rim 36 allows a variety of different devices to be attached to the hub 30. For instance, a syringe with a tip having a complemental threaded luer lock tip could be attached directly to the hub 30.

Various different types of back flow valves or other accessories would also first be typically attached to the hub 30 that would prevent back flow of medications or other substances out of the catheter 30. After such a back flow device, the syringe or other device, such as an infusion pump, would typically then be attached. A cap can also be attached, such as for times when the catheter is not in use. Other infusion pumps might be suitable for direct attachment to the threaded rim 36 of the hub 30. It is also conceivable that a needle penetratable septum could be located within the hub 30 or made to attach to the hub 30, such that medications could be delivered through the catheter 20 by injection through a needle passing through the septum to gain access to an interior of the catheter 20.

The hub 30 and catheter 20 could generally have any form which is desired by the medical practitioner including both known prior art catheters and future catheters which might be invented in the future for gaining access into veins V or other body lumens for the delivery of medications or other substances into the body of the patient. The catheter 20 can be provided without modification and the retainer 10 configured to attach to the catheter 20. Alternatively, the retainer 10 can be built into the catheter 20 so that the catheter 20 is modified to include the retainer 10. Such integration of the catheter 20 with the retainer 10 could be by forming the catheter 20 along with the retainer 10, such as in a single molding procedure, or could be performed by adhesively bonding the retainer 10 to the catheter 20 or by utilizing a mechanical fastener to couple the retainer 10 to the catheter 20.

With continuing reference to FIGS. 1-8, particular details of the fixed sleeve 40, defining a preferred form of base portion of the retainer 10, are described according to this preferred embodiment. The base portion of the retainer 10 is either fixed to the catheter 20 in a removably attachable fashion or fixed to the catheter 20 in a permanent fashion, as described above. This fixed sleeve 40 is primarily described herein as being removably attachable to the catheter 20, with the option of formation with the catheter 20 also available, and without any particular preference for either variation.

The fixed sleeve 40 includes an attachment surface 42 which is preferably generally cylindrical and has a diameter which can receive a portion of the catheter 20 passing therethrough. An outer surface 43 is provided opposite the attachment surface 42 with a thickness of the fixed sleeve 40 defined by a distance between the outer sleeve 43 and the attachment surface 42. The attachment surface 42 has a diameter similar to, but slightly greater than, a diameter of the wall 24 of the catheter 20. As an alternative, the attachment surface 42 could be a slightly smaller diameter so that a somewhat friction fit occurs for requiring sufficient force to allow the catheter 40 to pass through the fixed sleeve 40.

The attachment surface 42 preferably includes teeth 44 extending inwardly therefrom. These teeth 44 engage the wall 24 of the catheter 20 slightly, further discouraging movement of the fixed sleeve 40 along the catheter 40. Most preferably, these teeth 44 are biased so that they allow the catheter 20 to be threaded into the fixed sleeve 40 more readily in a first direction than in a second direction.

In particular, the discharge end 28 would typically be fed through the fixed sleeve 40 in a direction first passing through a proximal end 45 of the fixed sleeve 40 closest to the expandable width portion of the retainer 10, in the form of the wings 60. The teeth 44 are biased to allow the discharge end 28 of the catheter 20 to more readily pass through the proximal end 45 of the fixed sleeve 40 and on through the fixed sleeve 40 to emerge out of the fixed sleeve 40. The catheter 20 can then be further pulled until a desired length of catheter 20 extends through the fixed sleeve 40.

The outer surface 43 of the fixed sleeve 40 preferably includes grooves 46 which are elongate and extend along a long axis of the catheter 20 when the fixed sleeve 40 has the catheter 20 passing therethrough. These grooves 46 are preferably provided in a pair which are circumferentially spaced from each other on opposite sides of the fixed sleeve 40. Most preferably, they are provided on what would generally be an upper side of the fixed sleeve 40 and an underside of the fixed sleeve 40. Upper and lower sides are defined with the entire catheter 20 typically oriented diagonally relative to the skin S so that an upper side of the fixed sleeve 40 and catheter 20 is closest to the skin S and an underside of the fixed sleeve 40 and catheter 20 is generally most distant from the skin S.

These grooves 46 are configured to receive tabs 56 on the sliding sleeve 50 as described in detail below. Such tabs 56 provide one means to encourage the teeth 44 to more securely grip the catheter 20, to affix the fixed sleeve 40 securely to the catheter 20. Alternatively, merely by biasing the teeth 44, the fixed sleeve 40 can be prevented from sliding along the catheter 20 when tugging forces are exerted on the catheter 20 tending to cause the catheter 20 to otherwise pass through an incision I in the skin S and out of the patient.

With continuing reference to FIGS. 1-8, particular details of the sliding sleeve 50 are described. The sliding sleeve 50 attaches to an end of the wings 60 opposite the fixed sleeve 40. The sliding sleeve 50 includes an inner end 52 opposite an outer end 54 with a bore 53 extending from the inner end 52 to the outer end 54, and with the bore 53 being generally cylindrical in form. The bore 53 preferably has a diameter similar to, but slightly greater than, a diameter of the wall 24 of the catheter 20. The sliding sleeve 50 is also located with the catheter 20 passing therethrough, and with the sliding sleeve 50 closer to the skin S than the fixed sleeve 40 when the catheter 20 and retainer 10 have been implanted within the patient at a subcutaneous location.

The sliding sleeve 50 has a sufficiently large diameter for the bore 53 so that the sliding sleeve 50 can translate linearly along the catheter 20 (along arrow A of FIG. 1) while the fixed sleeve 40 of the retainer 10 remains fixed to the catheter 20. The sliding sleeve 50 preferably includes tabs 56 extending from the inner end 52 thereof. These tabs 54 are aligned with the grooves 46 in the fixed sleeve 40. When the sliding sleeve 50 is slid towards the fixed sleeve 40, the tabs 56 are caused to slide into the grooves 46. This stabilizes the entire retainer 10, so that the sliding sleeve 50 resists any rotation relative to the fixed sleeve 40 or the catheter 20. Also, the tabs 56 exert a radial inward force on the fixed sleeve 40, causing the teeth 44 to grip the wall 24 of the catheter 20 more securely, so that the fixed sleeve 40 is even more securely held to the wall 24 of the catheter 20 when the sliding sleeve 50 is slid to a position adjacent the fixed sleeve 40.

With continuing reference to FIGS. 1-8, particular details of the wings 60, defining a preferred form of expandable width portion of the retainer 10, are described according to this preferred embodiment. The wings 60 in this embodiment include a plurality of links 62 hingedly attached to other links 62 of the wings 60 as well as to either the fixed sleeve 40 or sliding sleeve 50. While a single wing 60 having two links 62 could be provided, most preferably, a pair of wings 60 are provided with each of the wings 60 including two links 62 therein, and with the two wings 60 oriented on opposite sides of the catheter 20 when the retainer 10 is attached to the catheter 20, and with the wings 60 at intermediate circumferential locations between the tabs 56.

Each of the wings 60 preferably includes one link 62 hingedly coupled to the fixed sleeve 40 through a fixed hinge 64 and one link 62 hingedly coupled to the sliding sleeve 50 through a sliding hinge 66. A tip hinge 68 is provided between the pair of links 62 forming each wing 60. Each of these hinges 64, 66, 68 is provided so that the links 62 can pivot relative to each other and relative to the fixed sleeve 40 and sliding sleeve 50.

In particular, the wings 60 have a first collapsed configuration where the links 62 are parallel with each other and exhibit an elongate form parallel with a long axis of the catheter and a central axis of the fixed sleeve 40 and sliding sleeve 50. In this configuration, the sliding sleeve 50 is spaced from the fixed sleeve 40 by a distance equal to twice a length of each of the links 62. The two links 62 are typically of similar length.

When the links 62 pivot about the hinges 64, 66, 68, the links 62 rotate 90° and take on a position where the links 62 are adjacent to each other and extending perpendicular to a long axis of the catheter 20 and sleeves 40, 50. This expanded configuration is achieved with movement of the tip hinges 68 of the wings 60 along arrow D of FIG. 1. FIG. 2 shows the wings 60 fully transitioned to the expanded configuration. The wings 60 can return to the collapsed configuration by movement of the sliding sleeve 50 away from the fixed sleeve 40 to return the wings 60 to their collapsed configuration.

With continuing reference to FIGS. 1-8 details of the handle 70 are described according to this preferred embodiment. The handle 70 provides a preferred form of means to allow a medical practitioner to move the sliding sleeve 50 relative to the fixed sleeve 40 to cause the wings 60 to transition from the collapsed configuration to the expanded configuration. In particular, the handle 70 includes an elongate arm 74 coupled to the sliding sleeve 50 through a pivot joint 72. The arm 74 is formed of a semi-circular wall 76 which is hollow along a centerline thereof and does not completely surround the centerline. The arm 74 has a free end 78 opposite the pivot joint 72.

The semi-circular wall 76 preferably is slightly more than 180° in circumferential extension around a centerline of the handle 70. Also, a diameter of the semi-circular wall 76 is preferably similar to a diameter of the wall 24 of the catheter 20. Thus, the handle 70 can be pivoted towards the catheter 20 (along arrow C of FIG. 2) and the semi-circular wall 76 can snap onto the catheter 20 to hold the handle 70 against the catheter 20.

Preferably, a length of the arm 74 between the pivot joint 72 and the free end 78 is similar to a length of the catheter 20 between the step 32 in the hub 30 and the outer end 54 of the sliding sleeve 50 after the sliding sleeve 50 has been moved to a position adjacent the fixed sleeve 40, and with the wings 60 in their extended position. In this way, the handle 70 can keep the sliding sleeve 50 from sliding away from the fixed sleeve 40 when the handle 70 has been clamped onto the catheter 20 and abutting the step 32 in the hub 30. One way to cause the arm 74 to have the proper length, especially when the fixed sleeve 40 is able to slide relative to the catheter 20, is to make the arm 74 extra long, and adapted to be trimmed in length after expansion of the wings 60.

Other locks or fasteners could alternatively be provided to secure the handle 70 to portions of the catheter 20 outside of the skin S. For instance, a clamp could be provided to temporarily fasten the handle 70 to the catheter 20 and keep the handle 70 from sliding relative to the catheter 20. Also, some form of clasp could be provided between the hub 30 and the handle 70. Such a clasp could be extendible in length to various different lengths to accommodate the fixed sleeve 40 possibly at various different locations along the catheter 20 or to accommodate different preferences for a medical practitioner for an amount of the catheter 20 extending outside of the skin S. If the fixed sleeve 40 is permanently attached to the catheter 20, the handle 70 can be given a length which is similar to a distance from the proximal end 45 of the fixed sleeve 40 to the step 32 in the hub 30, minus a length of the sliding sleeve 50. With such sizing, the handle 70 would always be exactly as long as required to just fit inside of the step 32 in the hub 30, when the retainer 10 is in the expanded configuration.

In use and operation, and with particular reference to FIGS. 1 and 2, particular details associated with the use of the retainer 10 are described according to this preferred embodiment. Initially, if the retainer 10 is provided separate from the catheter 20, the catheter 20 is first threaded through the fixed sleeve 40 and sliding sleeve 50 of the retainer 10 until the catheter 20 is positioned where desired within the fixed sleeve 40. If the catheter 20 is formed with the retainer 10 already attached thereto, this first step is not required.

A medical practitioner then makes appropriate incisions at the incision point I in the skin S, through tissues T underneath the skin S, and at the entry point P into the vein V or other body lumen. The medical practitioner can then thread the catheter 20 and retainer 10 through the skin S at the incision I, through the tissue T, into the vein V or other lumen at the entry point P, and further into the vein V until the discharge end 28 of the catheter 20 is positioned where desired intralumenally and the retainer 10 is positioned where desired subcutaneously.

The medical practitioner is now ready to transition the retainer 10, with the expandable width portion transitioning from the collapsed configuration to the expanded configuration. During placement of the catheter 20 beneath the skin S, the expandable width portion in the form of the wings 60 would be in their collapsed configuration with the links 62 of the wings 60 parallel to each other and aligned with a central axis of the fixed sleeve 40, sliding sleeve 50 and catheter 20. The user then pushes the sliding sleeve 50 toward the fixed sleeve 40. Such sliding is preferably caused to occur by pushing on the handle 70 in a direction parallel with the catheter 20, and generally along arrow A (FIG. 1) to cause the sliding sleeve 50 to move toward the fixed sleeve 40. This motion causes the tip hinges 68 of the wings 60 to move away from each other and laterally away from a central axis of the catheter 20 (along arrow D of FIG. 1) as the links 62 of the wings 60 rotate. When the fixed sleeve 40 and the sliding sleeve 50 abut each other, the wings 60 have been fully expanded (FIG. 2).

Because the sliding sleeve 50 must move towards the fixed sleeve 40 (along arrow A) the potential exists for the sliding sleeve 50 to pass entirely through the skin S. While such repositioning of the sliding sleeve 50 could be allowed, most preferably the sliding sleeve 50 remains partially subcutaneous and partially outside of the skin S. To maintain the sliding sleeve 50 in this position straddling the incision I, one of two techniques can be followed.

First, the sliding sleeve 50 could be provided with sufficient length so that it remains straddling the incision I, both before and after sliding of the sliding sleeve 50 along arrow A of FIG. 1. A second option is to first place the catheter 20 slightly further into the vein V or other lumen than the desired final position for the discharge end 28 of the catheter 20.

Then, as the handle 70 is manipulated to cause the sliding sleeve 50 to slide toward the fixed sleeve 40 (along arrow A of FIG. 1) the catheter 20 can be simultaneously pulled outward from the skin S (along arrow B of FIG. 1). Thus, in a affect the sliding sleeve 50 remains in fixed position relative to the skin S, and the catheter 20 and fixed sleeve 40 are instead brought towards the sliding sleeve 50.

Once the wings 60 have been transitioned fully to their expanded configuration (FIG. 2), the handle 70 is rotated (along arrow C of FIG. 2) until the clamp of the handle 70 snaps onto the catheter 20 and abutting the step 32 in the hub 30. If necessary, the handle 70 can be trimmed to fit snug against the step 32 in the hub 30. This step can also be altered to include a catch for the free end 78 of the handle 70, to cause the handle 70 to be securely held to the catheter 20 and prevent sliding of the sleeve 50. The sliding sleeve 50 is now held securely in place and the wings 60 have been deployed subcutaneously beneath the skin S. Should forces be further applied to the catheter 20 (such as along arrow B of FIG. 1), the wings 60 will resist such catheter motion because the wings 60 would impact an underside of the skin S and be too wide to pass through the incision I in the skin S.

When a medical practitioner desires to remove the catheter 20, the following procedure is followed. First, the handle 70 is snapped off of the catheter 20. Next, the handle 70 can be manipulated to cause the sliding sleeve 50 to slide away from the fixed sleeve 40. Once the wings 60 have fully transitioned to their collapsed configuration, the medical practitioner can pull on the catheter 20 (along arrow B) and remove both the catheter 20 and the retainer 10 through the incision I and out of their subcutaneous position. The catheter 20 would also be removed from the vein V. If necessary, stitches or other closure devices could be utilized to close the vein V and/or skin S where the catheter 20 had previously penetrated these body structures.

Figure 9:
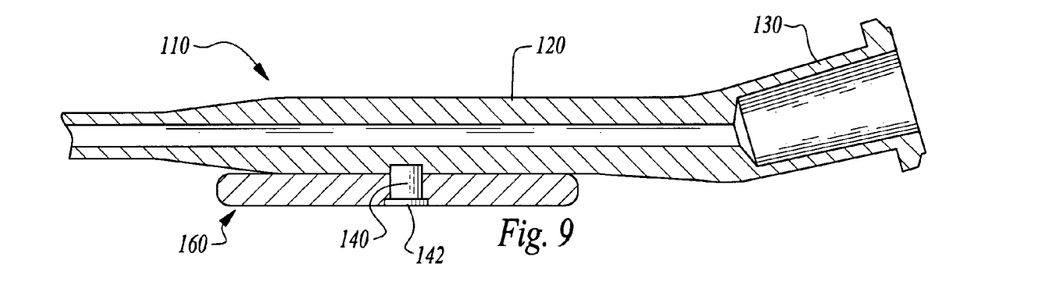
FIG. 9 is a full sectional view of a first alternative embodiment of the subcutaneous medical tube retainer of this invention, with the retainer in the form of a post extending from a catheter or other medical tube, and with a leg pivotably attached to the post shown in a collapsed form.
Figure 10:
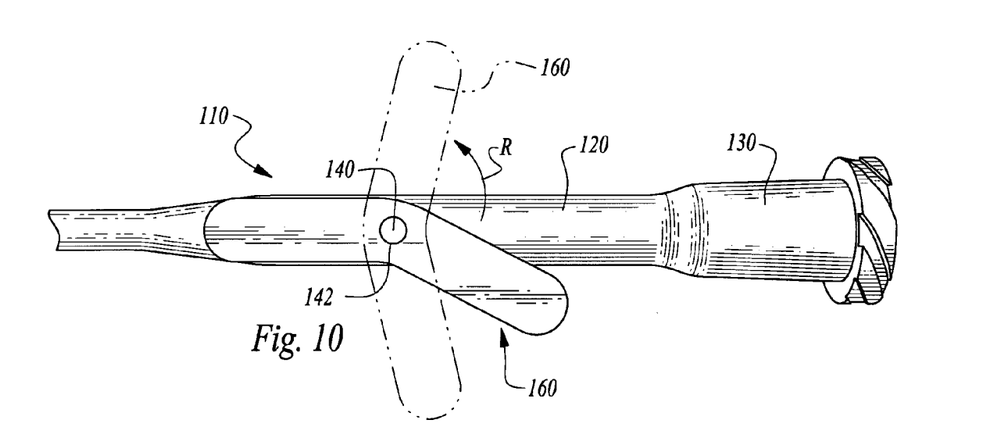
FIG. 10 is a bottom plan view of that which is shown in FIG. 9 and showing the leg in collapsed form and with the leg also shown in expanded form in phantom.

With particular reference to FIGS. 9 and 10, details of a first alternative catheter retainer 110 are described. The catheter retainer 110 is similar to the retainer 10 and catheter 20 of the preferred embodiment except as particularly described herein. The catheter retainer 110 includes a catheter 120 which preferably has a wall thickness which increases slightly near a location where the retainer 110 is located. The catheter 120 includes a hub 130 at an end thereof adapted to be positioned outside of the skin of the patient.

Uniquely, the retainer 110 includes a post 140 providing a preferred form of pivot acting as a base portion of the retainer 110. This post 140 is preferably substantially cylindrical and oriented perpendicular to a central axis of the catheter 120. The post 140 preferably terminates at a cap 142 spaced from the catheter 120. The post 140 can be formed with the catheter 120 or bonded to the catheter 120 or caused to mechanically attach to the catheter 120, such as by threading into a hole formed in the catheter 120 or be press-fitting into a bore extending a short distance into the catheter 120.

The post 140 is securely affixed to the catheter 120 to provide the base portion of the retainer 110 in this embodiment. The post 140 also acts as a pivot about which a leg 160 of the retainer 110 can rotate (about arrow R of FIG. 10). In particular, the leg 160 acts as the expandable width portion of the retainer 110 in this embodiment. This leg 160 is preferably substantially rigid and elongate in form extending from a first end 162 to a second end 164. Most preferably, a bend 166 is provided adjacent the post 140 such that the leg 160 has portions adjacent the first end 162 slightly out of an in-line arrangement with portions of the leg 160 adjacent the second end 164. For instance, the bend 166 can result in approximately a 30° angle away from parallel for the portions of the leg 160 on either side of the bend 166.

Most preferably, the post 140 extends downwardly from a bottom of the catheter 120. FIG. 10 depicts a bottom plan view of the catheter retainer 110. The leg 160 is adapted to rotate preferably slightly greater than 90° to a final position which is bilaterally symmetrical relative to a central plane of the catheter 120. Before the leg 160 is rotated it is considered to be in its collapsed configuration for the catheter retainer 110. After rotation along arrow R (FIG. 10 and depicted in phantom), the leg 160 has transitioned into its expanded configuration.

The leg 160 would be provided in its collapsed configuration during implanting of the catheter 120 along with the associated catheter retainer 110. After positioning of the catheter 120 has occurred, the leg 160 is then rotated (along arrow R) to transition the leg 160 to the expanded position so that the retainer 120 can function to keep the catheter 120 from being removed from its implanted location.

Such rotation of the leg 160 could occur by having a line of some kind coupled to one end of the leg 160 which could then be pulled to cause the leg 160 to rotate. Alternatively, some form of medical instrument could be passed through the incision I (FIG. 1) and caused to manipulate the leg 160 to rotate the leg 160 between the collapsed position and the expanded position. If desired, detents could be provided to encourage the leg 160 to snap into its collapsed position and to snap into its expanded position, such that the leg 160 would not be easy to rotate between the collapsed position and the expanded position inadvertently. The collapsed position for the leg 160 can also be referred to as a narrow form for the leg 160 with the expanded configuration referred to as a wide form for the leg 160.

Figure 11:
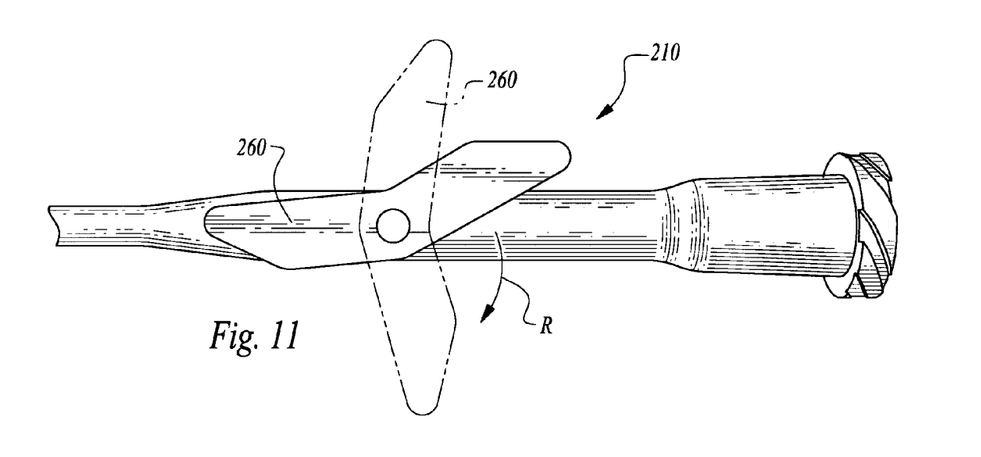
FIG. 11 is a bottom plan view of an alternative embodiment of that which is shown in FIG. 10.

With particular reference to FIG. 11, a second alternative catheter retainer 210 is described. This second alternative catheter retainer 210 is similar to the first alternative catheter retainer 110 (FIGS. 9 and 10) except that a faceted leg 260 is provided pivotably attached to the second alternative catheter retainer 210. The faceted leg 260 is slightly more streamlined during the implanting process while still having a bend therein, and may in some instances be easier to pivot (along arrow R of FIG. 11) between the collapsed position (depicted in solid lines) and the expanded configuration (depicted in phantom).

Figure 12:
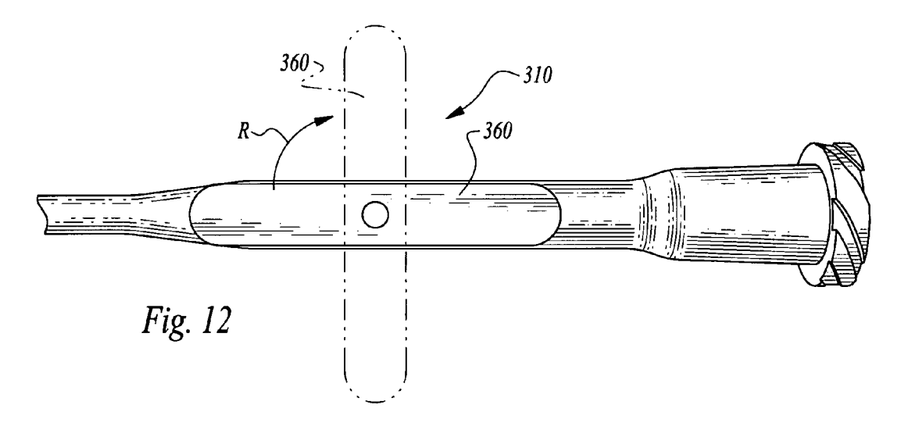
FIG. 12 is a bottom plan view of another alternative embodiment of that which is shown in FIG. 10.
Figure 13:
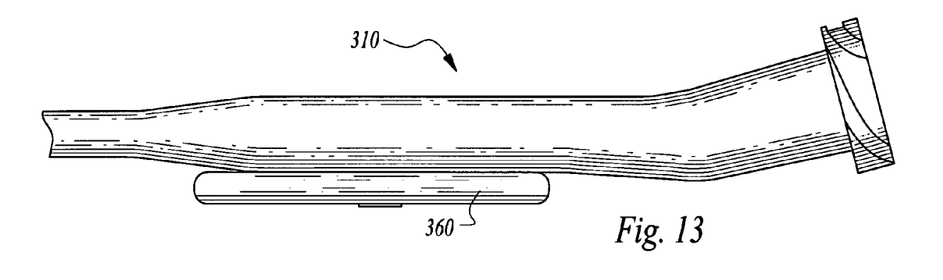
FIG. 13 is a side elevation view of that which is shown in FIG. 12.

With particular reference to FIG. 12, details of a third alternative catheter retainer 310 are described. The third alternative catheter retainer 310 is similar to the first and second alternative catheter retainers 110, 210, except that a straight leg 360 is provided. This straight leg 360 provides the simplest form of pivoting expandable width portion for the retainer 310. This third alternative catheter retainer 310 is also depicted in FIG. 13, and illustrates how the straight leg 360 can maintain a low profile along with the catheter to maximize an ease of implantation of the catheter along with the catheter retainer 310.

Figure 14:
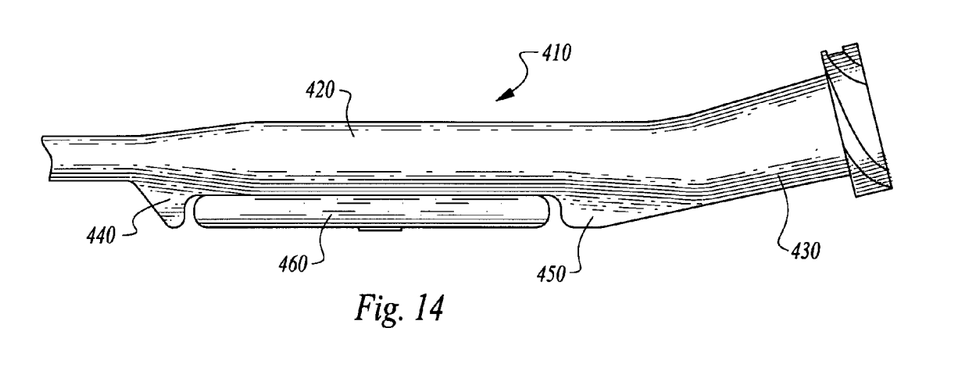
FIG. 14 is a side elevation view of an alternative embodiment of that which is shown in FIGS. 12 and 13 and showing how ramps can be provided on the catheter adjacent to a location where the leg of this embodiment is provided.

With particular reference to FIG. 14, details of a fourth alternative catheter retainer 410 are described. This fourth alternative catheter retainer 410 is similar to the third alternative catheter retainer 310 except that ramps 440, 450 are provided to further enhance a streamlined form for the catheter 420 and associated fourth alternative catheter retainer 410. In particular, a first ramp 440 is provided adjacent one end of the leg 460 and the second ramp 450 is provided adjacent an opposite end of the leg 460 from the first ramp 440. These ramps 440, 450 are attached to the catheter 420 and have a height similar to a thickness of the leg 460.

The ramps 440, 450 have a sloping side on a portion thereof facing away from the leg 460. These ramps facilitate smooth insertion of the catheter 420 and associated catheter retainer 410 through the incision I (FIG. 1) and otherwise through tissues T (FIGS. 1 and 2) in a subcutaneous environment. In particular, the first ramp 440 would be beneficial for streamlining the catheter 420 during insertion of the catheter 420. The second ramp 450 would be useful in streamlining the catheter 420 during removal of the catheter 420. In this embodiment the hub 430 is also slightly modified to accommodate the second ramp 450.

Figure 15:
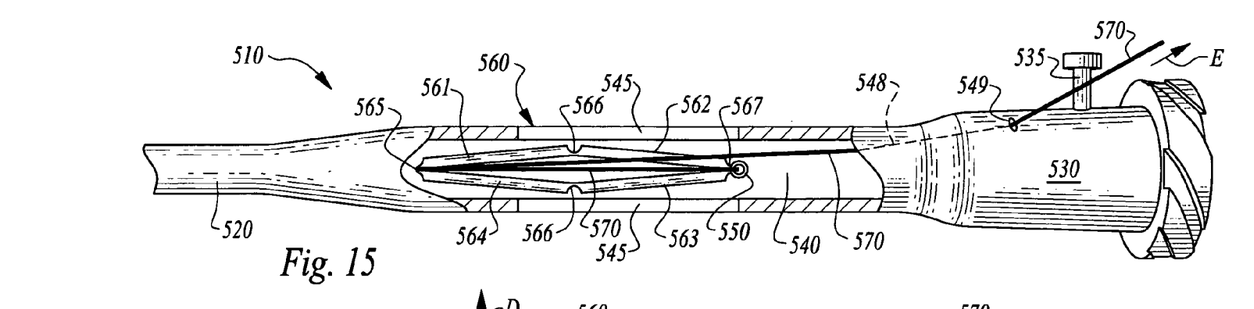
FIG. 15 is a bottom plan view of a fifth alternative embodiment subcutaneous medical tube retainer according to this invention and with portions thereof cut away to reveal an interior chamber and expandable width portion of the retainer located within the chamber and shown in a collapsed configuration.
Figure 16:
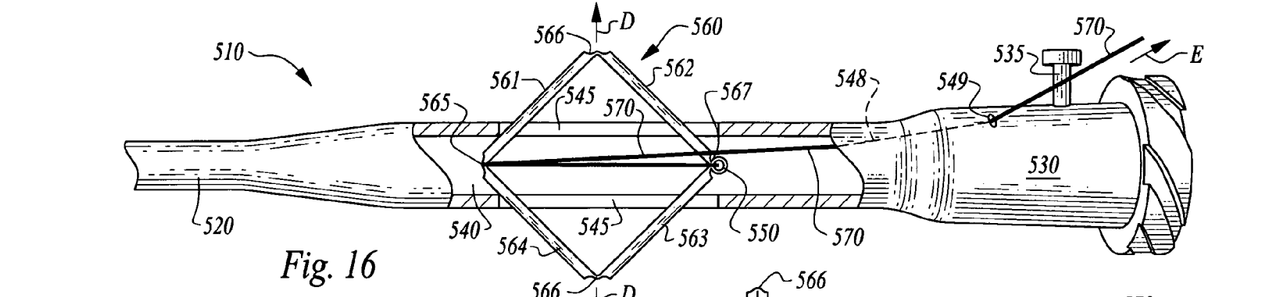
FIG. 16 is a bottom plan view similar to that which is shown in FIG. 15, but with the expandable width portion transitioning between the collapsed configuration and the expanded configuration.
Figure 17:
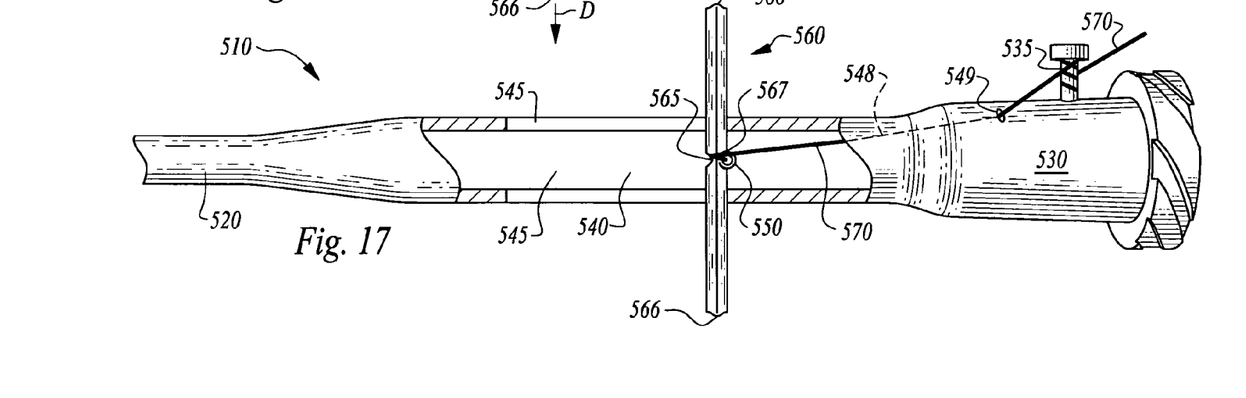
FIG. 17 is a bottom plan view similar to that which is shown in FIGS. 15 and 16, but with the expandable width portion shown fully transitioned to the expanded configuration.

With particular reference to FIGS. 15-17, details of a fifth alternative catheter retainer 510 are described. In this fifth alternative catheter retainer 510, a catheter 520 is provided generally similar to the catheter 20 of the preferred embodiment except that a lower portion of the catheter 20 is enlarged on a lower side and fitted with a lower chamber 540 and walls surrounding this lower chamber 540. FIGS. 15-17 show the fifth alternative catheter retainer 510 and catheter 520 in bottom plan views to show the details of this lower chamber 540. Upper portions of the catheter 520 would merely include a cylindrical conduit passing therethrough for passage of medications or other substances through the catheter 520. This conduit does not in any way interact with the lower chamber 540 or otherwise interact with the fifth alternative catheter retainer 510, and so this conduit is not depicted in FIGS. 15-17 (or the following embodiment of FIGS. 18 and 19).

The catheter 520 includes a hub 530 at an end thereof adapted to remain outside of the skin of the patient. A knob 535 is located on the hub 530 to interact with a pull line 570 described in further detail below.

The lower chamber 540 is preferably a hollow structure defined by surrounding rigid walls. The lower chamber 540 is preferably entirely enclosed by these walls, except where side slots 545 extend laterally out each side of the catheter 520. A tunnel 548 also preferably extends from the lower chamber 540 and out of the hub 530 at an opening 549 near the knob 535 for routing of the pull line 570 as described in detail below.

An expansion loop 560 is positioned within the lower chamber 540 and preferably fixed in position at an anchor 550 affixed to portions of the catheter 520 adjacent the lower chamber 540. This anchor 550 can be in the form of a post extending vertically downward. The expansion loop 560 acts as a preferred form of expandable width portion of the fifth alternative catheter retainer 510. The anchor 550 acts as a base portion of the fifth alternative catheter retainer 510.

The expansion loop 560 preferably includes four elongate segments including a first segment 561, second segment 562, third segment 563 and fourth segment 564. These segments 561, 562, 563, 564 are preferably joined together at a free joint 565 most distant from the anchor 550, a fixed joint 567 located at the anchor 550 and side joints 566 at intermediate locations between the free joint 565 and the fixed joint 567. The joints join ends of each of the segments 561, 562, 563, 564 together.

The pull line 570 is preferably coupled to the free joint 560 so that when the pull line 570 is pulled (along arrow E of FIGS. 15 and 16) the free joint 565 can be pulled toward the fixed joint 567. When such transition occurs on the expansion loop 560, portions of the segments 561, 562, 563, 564 extend out through the side slots 545. The side joints 566 extend laterally (along arrow D of FIG. 16) to define a maximum width portion of the expansion loop 560 when in its expanded configuration.

While the anchor 550 preferably remains fixed, the expansion loop 560 could float within the lower chamber 540 and the pull line 570 could be routed from the floating anchor 550 at the fixed joint 567, to the free joint 565 and then back through the tunnel 548 to the outlet hole 549.

After the pull line 570 has been pulled (along arrow E of FIGS. 15 and 16) and the expansion loop 560 has fully transitioned to its expanded configuration, the pull line 570 would be wrapped about the knob 535 to tie off the pull line 570 and keep the expansion loop 560 in its expanded configuration. The joints 565, 566, 567 could be slightly spring loaded so that the expansion loop 560 can be returned to its collapsed configuration merely be removing the pull line 570 from the knob 535 or by cutting the pull line 570. These spring forces would then cause the expansion loop 560 to automatically transition back to its collapsed configuration.

Alternatively, some form of medical instrument could be utilized through the incision I (FIG. 1) to encourage portions of the expansion loop 560 which have passed through the side slots 545 back into the lower chamber 540, so that the catheter 520 and associated fifth alternative catheter retainer 510 could be removed out of the incision I when use of the catheter 520 is no longer required. While the expansion loop 560 is shown with four segments, it is conceivable that the expansion loop 560 could include just two segments that would extend out of only one of the two side slots 545 or if desired, only one side slot 545 could be provided. Also, it is conceivable that an elongate leg similar to that shown in FIGS. 9-14 could be located within the lower chamber 540 and caused to pivot about an appropriate post into and out of the side slots 545 to act as the expandable width portion.

Figure 18:
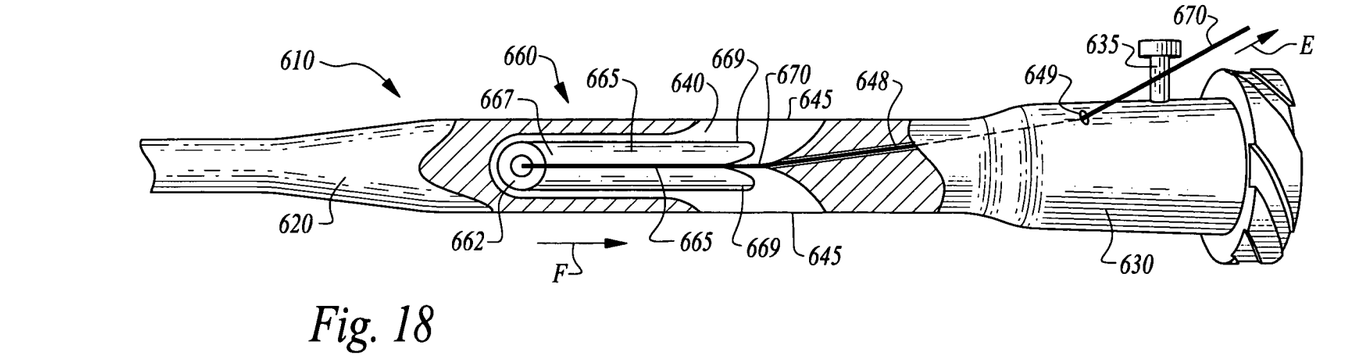
FIG. 18 is a bottom plan view of a sixth alternative embodiment of the subcutaneous medical tube retainer of this invention with portions cut away to reveal details of the chamber and an alternative expandable width portion contained within the chamber, with the expandable width portion in the form of an expansion shuttle shown in a collapsed configuration.
Figure 19:
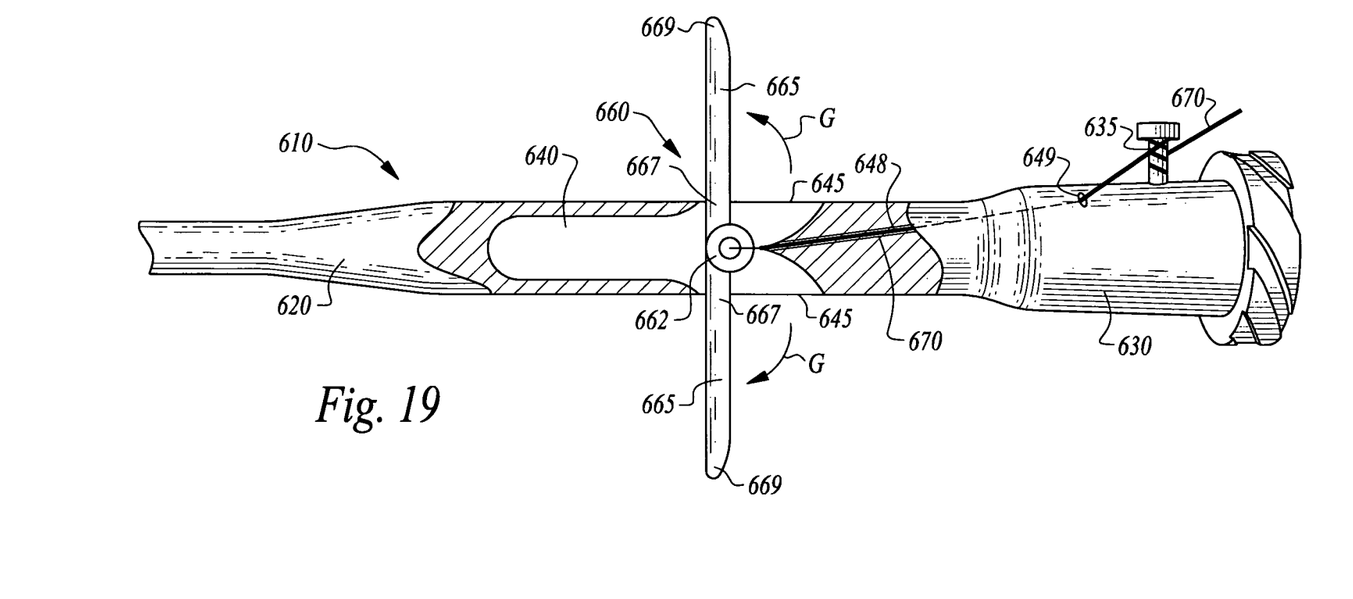
FIG. 19 is a bottom plan view similar to that which is shown in FIG. 18, but with the expansion shuttle shown fully transitioned to an expanded configuration.

With particular reference to FIGS. 18 and 19, particular details of a sixth alternative catheter retainer 610 are described. In this embodiment, the catheter 620 includes a hub 630 and knob 635 similar to those depicted with the fifth alternative catheter retainer 510 of FIGS. 15-17. A lower chamber 640 is again provided on a lower portion of the catheter 620 and in position avoiding interference with the conduit of the catheter 620 in a manner similar to that described above with the catheter 520 of the fifth alternative catheter retainer 510 (FIGS. 15-17). The lower chamber 640 is preferably slightly altered in geometry to accommodate the unique expandable width portion of the sixth alternative catheter retainer 610. In particular, the side ports 645 are not generally centered at a midpoint of the lower chamber 640, but rather are located closer to the hub 630 on the catheter 620. A tunnel 648 and outlet hole 649 are provided similar to those described above with respect to the fifth alternative catheter retainer 510 (FIGS. 15-17).

With the sixth alternative catheter retainer 610, the expandable width portion is preferably in the form of an expansion shuttle 660. This expansion shuttle 660 is configured to both translate and change configuration while transitioning between a collapsed configuration and an expanded configuration. In particular, the expansion shuttle 660 includes a hinged body 662 at which a pair of limbs 665 are pivotally attached together. Each limb 665 has a root 667 adjacent the hinged body 662 and a tip 669 opposite the root 667.

A pull line 670 is coupled to the hinged body 662 and is routed through the tunnel 548, similar to the routing of the pull line 570 of the fifth alternative catheter retainer 510 (FIGS. 15-17). When the pull line 670 is pulled (along arrow E of FIG. 18), the entire expansion shuttle 660 is caused to move toward the hub 630 (along arrow F). Curving surfaces on the tips 669 of each limb 665 interact with curving surfaces in the lower chamber 640 as the expansion shuttle 660 moves towards the hub 630, causing the limbs 665 to rotate and extend out of the side ports 645 (along arrow G). Once the hinged body 662 has fully transitioned to a final position resting within the lower chamber 640 at a side of the lower chamber 640 closest to the hub 630, the limbs 665 have been rotated until they extend lateral to a long axis of the catheter 620 and are fully within the expanded configuration.

Once the expansion 660 has been fully transitioned to its expanded configuration, the pull line 670 can be wrapped about the knob 635 to keep the expansion shuttle 660 in this expanded configuration. The hinged body 662 can be spring loaded to exert rotating forces upon the limbs 665 giving them a bias towards being located adjacent each other. With such a spring loading of the hinged body 662, merely cutting the pull lines 670 or removing the pull lines 670 from the knobs 635 will cause the expansion shuttle 660 to return to its original and collapsed configuration totally contained within the lower chamber 640.

As an alternative, the expansion shuttle 660 could be returned to its original collapsed configuration within the lower chamber 640 by moving the catheter 620 into the body somewhat, against tissue T (FIGS. 1 and 2) to impact upon the limbs 665 and cause them to rotate (in a direction opposite that depicted by arrow G of FIG. 19) and cause the entire expansion shuttle 660 to collapse and return back into the lower chamber 640. A medical practitioner can then use an appropriate medical instrument to cover the side ports 645 while removing the catheter 620, so that the tip 669 of the limbs 665 do not catch on tissues T or the skin S (FIGS. 1 and 2) as the catheter 620 is removed through the incision I (FIG. 1).

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. For instance, while catheters are primarily shown and described, this invention also covers modifications to accommodate vascular access sheaths, cannulas and any other medical tubes adapted to go into a body cavity at a discharge end and out of the skin S at an access end. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for retaining a skin penetrating medical tube at an implant site, the method including the steps of:
    selecting a retainer including a base portion attached to a subcutaneous portion of a medical tube spaced from a discharge end of the medical tube; an expandable width portion adapted to be coupled to the base portion; and the expandable width portion having at least two configurations including an expanded configuration with a width greater than the base portion, and a collapsed configuration with a width less than the width of the expanded configuration, the retainer attached to the medical tube;
    implanting the medical tube with the distal discharge end penetrating a body lumen or vessel and adapted to transfer fluids between the body lumen and the medical tube, with the retainer outside of the body lumen or vessel that the medical tube penetrates and below the skin; and
    transitioning the expandable width portion of the retainer from the collapsed configuration to the expanded configuration with the expandable width portion below the skin and outside of the body lumen or vessel that the medical tube penetrates;
    wherein said implanting step includes the steps of:
        forming an opening in the skin;
        forming an opening in a body lumen;
        routing the implanted end of the medical tube through the opening in the skin and through the opening in the lumen with the medical tube having the implanted end located inside the body lumen and an access end opposite the implanted end located outside of the body, and with the retainer between the skin and the body lumen;
    wherein said selecting step includes the base portion of the retainer configured to include a fixed sleeve adapted to at least partially surround the subcutaneous portion of the medical tube and be affixed to the medical tube at a location on the medical tube spaced from the discharge end and outside of the body lumen, the retainer including a sliding sleeve having a bore with a portion of the medical tube routed through the bore, the sliding sleeve adapted to slide along the medical tube, and with an expandable width wing interposed between the sliding sleeve and the fixed sleeve;
    the further step of sliding the sliding sleeve toward the fixed sleeve to transition the retainer from a narrower form to a wider form, such that the expandable width portion is transitioned from the collapsed configuration to the expanded configuration beneath the skin and outside of the body lumen; and
    wherein said sliding sleeve includes a pair of tabs extending toward said fixed sleeve, and wherein said fixed sleeve includes a pair of grooves, said grooves at least as wide as said tabs, said tabs sliding into said grooves during said sliding step.

2. The method of claim 1 wherein said selecting step includes the retainer mechanically affixed to the medical tube.

3. The method of claim 1 wherein said selecting step includes the retainer bonded to the medical tube.

4. The method of claim 1 wherein said selecting step includes the retainer formed along with the medical tube during a medical tube forming process.

5. The method of claim 1 including the further step of configuring the sliding sleeve to include a handle extending therefrom, said handle having an elongate form with a distal end coupled to said sliding sleeve and a proximal end adapted to be gripped by a user to hold said sliding sleeve in position while said fixed sleeve and said medical tube are drawn toward said sliding sleeve during said sliding step.

6. The method of claim 5 wherein said sliding step includes the step of pulling on a proximal end of the medical tube while holding the sliding sleeve stationary to cause expansion of the retainer, with said discharge end of the medical tube remaining within the body lumen.

7. The method of claim 6 wherein said sliding step includes using the handle to keep the sliding sleeve at a transcutaneous position during said sliding step.

8. A method for retaining a skin penetrating medical tube at an implant site, the method including the steps of:
    selecting a retainer including a base portion attached to a subcutaneous portion of a medical tube spaced from a discharge end of the medical tube; an expandable width portion adapted to be coupled to the base portion; and the expandable width portion having at least two configurations including an expanded configuration with a width greater than the base portion, and a collapsed configuration with a width less than the width of the expanded configuration, the retainer attached to the medical tube;

implanting the medical tube with the distal discharge end penetrating a body lumen or vessel and adapted to transfer fluids between the body lumen and the medical tube, with the retainer outside of the body lumen or vessel that the medical tube penetrates and below the skin; and transitioning the expandable width portion of the retainer from the collapsed configuration to the expanded configuration with the expandable width portion below the skin and outside of the body lumen or vessel that the medical tube penetrates;

wherein said implanting step includes the steps of:
 forming an opening in the skin;
 forming an opening in a body lumen;
 routing the implanted end of the medical tube through the opening in the skin and through the opening in the lumen with the medical tube having the implanted end located inside the body lumen and an access end opposite the implanted end located outside of the body, and with the retainer between the skin and the body lumen;

wherein said selecting step includes the base portion of the retainer configured to include a fixed sleeve adapted to at least partially surround the subcutaneous portion of the medical tube and be affixed to the medical tube at a location on the medical tube spaced from the discharge end and outside of the body lumen, the retainer including a sliding sleeve having a bore with a portion of the medical tube routed through the bore, the sliding sleeve adapted to slide along the medical tube, and with an expandable width wing interposed between the sliding sleeve and the fixed sleeve;

the further step of sliding the sliding sleeve toward the fixed sleeve to transition the retainer from a narrower form to a wider form, such that the expandable width portion is transitioned from the collapsed configuration to the expanded configuration beneath the skin and outside of the body lumen;

configuring the sliding sleeve to include a handle extending therefrom, said handle having an elongate form with a distal end coupled to said sliding sleeve and a proximal end adapted to be gripped by a user to hold said sliding sleeve in position while said fixed sleeve and said medical tube are drawn toward said sliding sleeve during said sliding step; and wherein a pivot joint is provided between said handle and said sliding sleeve to facilitate pivoting of said handle relative to said sliding sleeve.

9. A method for retaining a skin penetrating medical tube at an implant site, the method including the steps of:

selecting a retainer including a base portion attached to a subcutaneous portion of a medical tube spaced from a discharge end of the medical tube; an expandable width portion adapted to be coupled to the base portion; and the expandable width portion having at least two configurations including an expanded configuration with a width greater than the base portion, and a collapsed configuration with a width less than the width of the expanded configuration, the retainer attached to the medical tube;

implanting the medical tube with the distal discharge end penetrating a body lumen or vessel and adapted to transfer fluids between the body lumen and the medical tube, with the retainer outside of the body lumen or vessel that the medical tube penetrates and below the skin; and transitioning the expandable width portion of the retainer from the collapsed configuration to the expanded configuration with the expandable width portion below the skin and outside of the body lumen or vessel that the medical tube penetrates;

wherein said implanting step includes the steps of:
 forming an opening in the skin;
 forming an opening in a body lumen;
 routing the implanted end of the medical tube through the opening in the skin and through the opening in the lumen with the medical tube having the implanted end located inside the body lumen and an access end opposite the implanted end located outside of the body, and with the retainer between the skin and the body lumen;

wherein said selecting step includes the base portion of the retainer configured to include a fixed sleeve adapted to at least partially surround the subcutaneous portion of the medical tube and be affixed to the medical tube at a location on the medical tube spaced from the discharge end and outside of the body lumen, the retainer including a sliding sleeve having a bore with a portion of the medical tube routed through the bore, the sliding sleeve adapted to slide along the medical tube, and with an expandable width wing interposed between the sliding sleeve and the fixed sleeve;

the further step of sliding the sliding sleeve toward the fixed sleeve to transition the retainer from a narrower form to a wider form, such that the expandable width portion is transitioned from the collapsed configuration to the expanded configuration beneath the skin and outside of the body lumen;

configuring the sliding sleeve to include a handle extending therefrom, said handle having an elongate form with a distal end coupled to said sliding sleeve and a proximal end adapted to be gripped by a user to hold said sliding sleeve in position while said fixed sleeve and said medical tube are drawn toward said sliding sleeve during said sliding step;

wherein said sliding step includes the step of pulling on a proximal end of the medical tube while holding the sliding sleeve stationary to cause expansion of the retainer, with said discharge end of the medical tube remaining within the body lumen;

wherein said sliding step includes using the handle to keep the sliding sleeve at a transcutaneous position during said sliding step; and rotating the handle about a pivot joint provided between said handle and said sliding sleeve to move the handle against a proximal end of the medical tube and securing the handle to the proximal end of the medical tube to secure the retainer in the expanded configuration.

10. The method of claim 9 wherein the proximal end of the medical tube includes a hub at the proximal end having greater width than portions of said medical tube extending distally from the hub, the handle abutting against the hub at an end of the handle opposite the sliding sleeve so that the handle prevents the sliding sleeve from sliding toward the hub at the proximal end of the medical tube by the handle interposed therebetween.

11. The method of claim 9 wherein the fixed sleeve is fixed to the medical tube with teeth extending inward from an inwardly facing attachment surface, the teeth engaging the medical tube to hold the fixed sleeve to the medical tube.

12. The method of claim 11 wherein the teeth are biased to resist fixed sleeve motion relative to the medical tube to a grater extent when pulling said proximal end of said medical tube relative to said handle and said sliding sleeve, than when forces are applied in an opposition direction.

13. The method of claim 12 wherein the biasing of the teeth includes the teeth having a shape with a proximal side more sloped than a distal side.

\* \* \* \* \*